United States Patent [19]

Hengartner

[11] 4,111,951
[45] Sep. 5, 1978

[54] PROCESS FOR L-3,4-DEHYDROPROLINE

[75] Inventor: Urs Oskar Hengartner, Roseland, N.J.

[73] Assignee: Hoffmann-La Roche Inc., Nutley, N.J.

[21] Appl. No.: 759,702

[22] Filed: Jan. 17, 1977

[51] Int. Cl.$^2$ .......................................... C07D 207/22
[52] U.S. Cl. .................................. 260/326.2; 424/274
[58] Field of Search ...................... 260/DIG. 8, 326.2

[56] References Cited

U.S. PATENT DOCUMENTS

| 2,528,267 | 10/1950 | Dearborn et al. | 260/DIG. 8 |
| 2,794,025 | 5/1957 | Amiard et al. | 260/326.2 |
| 2,984,684 | 5/1961 | Fike | 260/326.2 |

FOREIGN PATENT DOCUMENTS

| 750,156 | 6/1956 | United Kingdom | 260/DIG. 8 |
| 816,857 | 7/1959 | United Kingdom | 260/DIG. 8 |

OTHER PUBLICATIONS

Noller; Chemistry of Organic Compounds, pp. 341–346 (1959).
Chibata et al; Chem. Abs., vol. 84: 31454c, (1976).
Whitmore; Org. Chem. pp. 398–402 (1951).

*Primary Examiner*—Donald G. Daus
*Assistant Examiner*—Mary Vaughn
*Attorney, Agent, or Firm*—Samuel L. Welt; George M. Gould

[57] ABSTRACT

L-3,4-dehydroproline is produced in good yield from D,L-3,4-dehydroproline by resolution via the tartaric acid salt and thermal racemization of the D-3,4-dehydroproline tartaric acid salt containing mother liquors.

3 Claims, No Drawings

PROCESS FOR L-3,4-DEHYDROPROLINE

BACKGROUND OF THE INVENTION

The resolution of D,L-proline using (+) tartaric acid as the resolving agent in a water/ethanol system to afford L-proline has been described in Japanese Patent No. 75,101,355 issued Aug. 11, 1975, CA 84, page 505, abstract number 31494 C. However, the D-enantiomer cannot be thermally racemized.

DESCRIPTION OF THE INVENTION

The present invention relates to an improved process for the preparation of L-3,4-dehydroproline from D,L-diastereomer salt mixture with (+) tartaric acid, i.e., D-3,4-dehydroproline.(+) tartaric acid salt and L-3,4-dehydroproline (+) tartaric acid salt, selectively crystallizing out the L-3,4-dehydroproline.(+) tartaric acid salt, racemizing the D-3,4-dehydroproline.(+) tartaric acid salt remaining in the mother liquor by heat treatment selectively crystallizing out the additional L-3,4-dehydroproline.(+) tartaric acid salt thus formed and then decomposing the diastereomer to yield the desired L-proline. The product of the process, L-3,4-dehydroproline, is a patent collagenase inhibitor. It is also useful as a means of efficiently introducing deuterium or tritium labels into peptides by substituting for proline in such peptides and serving as substrate for catalytic deuteration or tritiation. See U.S. patent application Ser. No. 676,969, filed Apr. 14, 1976 now U.S. Pat. No. 4,041,023 for further details in this regard.

The first step of the present process involves the reaction of D,L-dehydroproline with an equimolar amount of (+) tartaric acid in water as sole solvent. It is preferable to utilize a concentrated solution of the reactants i.e., above 2 moles/liter and preferably about 5 moles/liter. At such concentrations it is necessary to heat the reaction medium to about 80° C. to effect solubilization. Upon cooling of the resulting solution L-3,4-dehydroproline.(+) tartaric acid salt crystallizes out and is collected.

The mother liquors from the above step is then heated at a temperature of 50° to 150° C. for 0.5 to 48 hours under an inert atmosphere to effectuate racemization of the D-3,4-dehydroproline.(+) tartaric acid salt contained in said mother liquor. After decolorization of the reaction medium, additional L-3,4-dehydroproline.(+) tartaric acid salt crystallizes out of the medium on cooling. A suitable inert atmosphere is selected from nitrogen, argon, helium, krypton or the like.

The combined crops of L-3,4-dehydroproline.(+) tartaric acid salt can be recrystallized and then the salt decomposed by means well known in the art. A preferred procedure is to utilize a cation exchange resin column with pyridine acetate elution. Monitoring of the elution fractions is accomplished by spotting a sample of each fraction on silica gel, spraying with ninhydrin and then developing at elevated temperature. The L-3,4-dehydroproline containing fractions produce a brown-orange spot on the gel.

The fractions providing a positive ninhydrin test are combined, the solvent removed and the product L-3,4-dehydroproline worked up in a conventional manner. A high overall yield of L-3,4-dehydroproline is obtained with excellent optical purity from D,L-3,4-dehydroproline.

The present invention is further illustrated by the following Examples. In such Examples the notation "e.e." means the enantiomeric excess as determined by chromatographic separation of L-Ala-L-$\Delta^3$-Pro and L-Ala-D-$\Delta^3$-Pro on an amino acid analyzer.

EXAMPLE 1

L-3,4-Dehydroproline (+) Tartaric Acid Salt

A 400ml beaker was charged with 56.6g (0.50 mol) of D,L-3,4-dehydroproline, 75.0g (0.50 mol) of (+) tartaric acid (Baker) and 110ml of water (distilled water is used throughout these examples). The mixture was stirred and heated at 80° C until all starting material was dissolved. The solution was stirred and allowed to cool to room temperature; at 48° the product began to crystallize. After the mixture had been stirred for three hours at room temperature and two hours in an ice bath, it was refrigerated overnight. The precipitate was collected on a glass sinter funnel (pre-cooled in the refrigerator), washed well with 2 × 50 ml = 100 ml of ice cold ethanol-water 1:1, 75ml of ice cold ethanol-water 2:1, and 75ml of ice cold ethanol and dried at room temperature (const. weight) to afford 52.3g (40%) of product as off-white crystals, mp 173° (dec); $[\alpha]_D^{25} = -114.7°$ (c = 1, 5N HCl); e.e. 99.5%+.

The washings of the above described filtration were collected in a separate suction flask and concentrated on a rotavap (water bath 40°; aspirator vacuum). The residual gum (24g) was taken up in 150ml of warm water and combined with the mother liquor. The brown solution was heated at reflux (oil bath 120°) under nitrogen for 9 hours. 20 g of charcoal (Norite SG-SV) was added, and the mixture was heated at reflux for 20 minutes and filtered through a bed of Celite which was washed with 50 ml of water. The deep yellow filtrate was concentrated on a rotavap (water bath 45°; aspirator vacuum). The residual orange-brown paste (92g) was dissolved in 50 ml of water at 70° and transferred into a beaker using an additional 12 ml of water to wash the flask. The warm solution was stirred for two hours at room temperature (when the temperature reached 40° the solution was seeded) and for two hours in an ice bath. The mixture was then refrigerated overnight. The precipitate was collected on a glass sinter funnel, washed with 2 × 25ml = 50 ml of ice cold ethanol-water 1:1, 40 ml of ice cold ethanol-water 2:1, and 40ml of ice cold ethanol and dried at room temperature (const. weight) to afford 25.5g (19%) of product as light orange crystals, mp 173° (dec); $[\alpha]_D^{25} = -114.0°$ (c = 1, 5N HCl); e.e. = 99.5%+. The two crops were dissolved in 100ml of water at 67°. Then 200ml of ethanol was added with stirring (soon thereafter crystallization of the product began). The mixture was stirred in a 20° water bath for one hour and was then refrigerated overnight. The precipitate was collected by filtration, washed with 120ml of ice cold ethanol and dried at room temperature (const. weight) to afford 71.5g (54%) of product as off-white crystals, mp 173° (dec); $[\alpha]_D^{25} = -115.0°$ (c = 1, 5N HCl); e.e. = 99.8%+.

A second crop was obtained by concentration of the mother liquor and recrystallization from water-ethanol (1:2) as described above: 3.8g (3%) of product as white crystals, mp 172° (dec); $[\alpha]_D^{25} = -114.5°$ (C = 1, 5N HCl).

EXAMPLE 2

L-3,4-Dehydroproline 70.0g (0.266 mol) of L-3,4-dehydroproline (+) tartaric acid salt (first crop material) was dissolved in 320ml of water at 25° and poured onto a 6.4cm (diameter) × 17.5cm (length) column of Dowex 50W - X4 cation exchange resin, 50–100 mesh (Biorad). The column was washed with a total of 1550ml of water. The product was then eluted with 2.4 l of 0.5M pyridine acetate which was collected in eight 300-ml fractions. Each fraction was spotted on Silica Gel, sprayed with ninhydrin and developed at elevated temperature. The fractions, 5,6 and 7 which contained the product showed a brown-orange spot. These three fractions were concentrated on a rotavap (water bath 25°, p = 1mm) and the residue was dissolved twice in 100ml of water and concentrated under the same conditions. The crystalline, wet residue (41.7g) was dissolved in 30ml of water. To the clear colorless solution was added with stirring over 30 minutes 240ml of ethanol (the solution was seeded after addition of the first 60ml). The mixture was refrigerated overnight. The precipitate was collected by filtration, washed with 50ml of ice cold ethanol and 100ml of ether and dried at room temperature/0.1mm to afford 25.3g (84%) of product as colorless needles, mp 244° (dec); $[\alpha]_D^{25} = 278.7°$ (c = 1, 5N HCl); $[\alpha]_D^{25} = -403.1°$ (c = 1, H$_2$O); e.e. 99.8%+. The mother liquor was concentrated on a rotavap (water bath 25°, aspirator vacuum) and the residue evaporated from 50ml of ethanol. The crystalline residue (4.6g) was dissolved in 9 ml of water and 40ml of ethanol was slowly added. The mixture was seeded, stirred at room temperature for one hour and refrigerated overnight. The precipitate was collected by filtration, washed with 10ml of ice cold ethanol, and 10ml of ether and dried at room temperature/0.1mm to afford an additional 2.7g(9%) of product as colorless crystals, mp 244° (dec); $[\alpha]_D^{25} = -278.8°$ (c = 1, 5N HCl); $[\alpha]_D^{25} = -404.3°$ (c = 1, H$_2$O); e.e. 99.8%+.

I claim:

1. An improved process for preparing L-3,4-dehydroproline from D,L-3,4-dehydroproline which process comprises the following steps in combination:
   (A) reacting D,L-3,4-dehydroproline with (+) tartaric acid in water to form the diastereomeric salts D-3,4-dehydroproline.(+) tartaric acid salt and L-3,4-dehydroproline.(+) tartaric acid salt;
   (B) selectively crystallizing the L-3,4-dehydroproline.(+) tartaric acid salt;
   (C) thermally racemizing the mother liquors from step (B) at a temperature in the range between about 50°–150° C so as to produce additional L-3,4-dehydroproline.(+) tartaric acid salt which is selectively crystallized; and
   (D) decomposing the L-3,4-dehydroproline.(+) tartaric acid produced in steps (B) and (C) so as to yield the desired L-3,4-dehydroproline.

2. The process of claim 1 wherein the reactants are present in a concentration of greater than 2-moles/liter and the reaction medium of step A is heated to 80° C to effectuate solution.

3. The process of claim 1 wherein the decomposition of the L-3,4-dehydroproline.(+) tartaric acid salt is accomplished by passing said salt through a cation exchange resin column.

* * * * *